United States Patent [19]

Sturm et al.

[11] 4,259,505

[45] Mar. 31, 1981

[54] PROCESS FOR THE PREPARATION OF 1H-AZOLE DERIVATIVES

[75] Inventors: Elmar Sturm, Aesch, Switzerland; Wolfgang Eckhardt, Lörrach, Fed. Rep. of Germany; Bernhard Gloor, Pratteln; Robert Nyfeler, Basle, both of Switzerland

[73] Assignee: Ciba-Geigy Corporation, Ardsley, N.Y.

[21] Appl. No.: 127,018

[22] Filed: Mar. 4, 1980

[51] Int. Cl.³ .................................... C07D 405/06
[52] U.S. Cl. .................................. 548/262; 548/336
[58] Field of Search ..................... 548/262; 548/336

[56] References Cited

U.S. PATENT DOCUMENTS 4,156,008  5/1979  Heeres .................................. 548/336

*Primary Examiner*—Alton D. Rollins
*Attorney, Agent, or Firm*—Karl F. Jorda

[57] ABSTRACT

An improved process for the preparation of 2-tert.-butyl-2-[1-phenoxy-1-(1H-azol-1-yl)]-methyl-ketales is disclosed, which process comprises reacting a 2-tert.-butyl-2-[1-phenoxy-1-halo]-methyl-ketale with a quaternary ammonium or phosphonium salt of an azole. The azoles used are 1H-1,2,4-triazole or 1H-imidazole.

14 Claims, No Drawings

PROCESS FOR THE PREPARATION OF 1H-AZOLE DERIVATIVES

DETAILED DISCLOSURE

This invention relates to an improved process for the preparation of compounds of the formula I

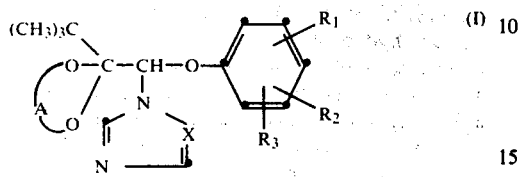

wherein
X represents —CH= or —N=;
R$_1$, R$_2$ and R$_3$ are each independently selected from the group consisting of hydrogen, halogen, lower alkyl, cyano, methoxy, phenyl and nitro;
A represents —CH(R$_4$)—CH(R$_5$)— or —CH$_2$—C(R$_6$)(R$_7$)—CH$_2$—;
R$_4$ and R$_5$ are each independently selected from the group consisting of hydrogen, C$_1$-C$_6$—alkyl, C$_1$-C$_6$—alkoxymethyl and phenoxymethyl or said substituents R$_4$ and R$_5$ form together a tetramethylene group; and R$_6$ and R$_7$ are each independently selected from the group consisting of hydrogen and lower alkyl.

These compounds are disclosed and claimed as valuable fungicides in Pat. Appl. Ser. No. 088,687 filed Oct. 26, 1979.

According to prior art practices the compounds of the above defined formula I were prepared by reaction of a compound II,

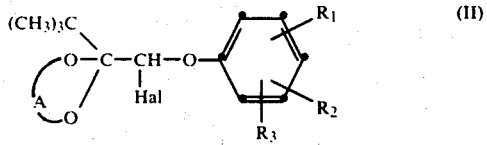

wherein A, R$_1$, R$_2$ and R$_3$ are as defined above and Hal represents a halogen atom, with a metal salt of 1H-1,2,4-triazole or 1H-imidazole in a polar solvent, preferably N,N-dimethylformamide, N,N-dimethylacetamide or dimethylsulphoxide.

However the practice of such a process entails distinct drawbacks and disadvantages with respect to yield as well as purity of the final product. In practice the necessity of using high temperatures during the mentioned process leads unavoidably to vast destruction of the molecule II, especially by loss of the phenoxy group.

The surprising discovery has now been made that azole derivatives of formula I can be prepared in high yields and high purity using low temperatures and short reaction times by the reaction of a quarternary salt of 1H-1,2,4-triazole or 1H-imidazole of the formula III,

wherein X represents —CH= or —N=; Z represents nitrogen or phosphorus; R$_8$, R$_9$, R$_{10}$ and R$_{11}$ are the same or different and are each independently selected from the group consisting of C$_1$-C$_{18}$-alkyl, aralkyl, aryl and aryloxyalkyl, with a compound of formula II.

In a narrower sense, the invention relates to an improved process for the preparation of compounds according to formula I, as defined above, by the reaction of an azolium anion of the formula

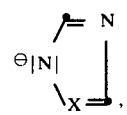

wherein X represents —CH= or —N=, with a compound of the formula II as defined above, which improvement comprises reacting said precursor compound II at a temperature of from 30° to 110° centigrades with an azolium anion of the formula III, as defined above, thereby splitting off a compound of the formula

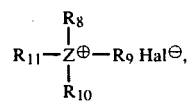

wherein Z, R$_8$, R$_9$, R$_{10}$, R$_{11}$ and Hal are as defined above.

Suitable quaternary ammonium salts are, such as, for examples: tetraethyl-, tetrapropyl-, tetrabutyl-, tetrapentyl-, tetrahexyl-, tetraheptyl-, tetraoctyl-, tetranonyl-, tetradecyl-, methyltributyl, dimethyldibutyl-, trimethylbutyl-, methyltrioctyl-, benzyltrimethyl-, benzyltriethyl-, benzyltripropyl-, benzyltributyl-, benzyldimethylhexadecyl-, benzyldimethylhexadecyl-, diisobutyl-cresoxyethyl-dimethylbenzyl-, trimethylphenyl-, diphenyldimethyl-, butyltripropyl-, tributylphenyl-, tricaprylmethyl-ammonium salts of 1H-1,2,4-triazole or 1H-imidazole.

Examples of suitable quaternary phosphonium salts are, such as: tetrapropyl-, tetrabutyl-, tetrapentyl-, methyltributyl-, benzyltrimethyl-, benzyltriphenyl-, ethyltriphenyl-, hexadecyltributyl-phosphonium salts of 1H-1,2,4-triazole or 1H-imidazole.

Preferred are the quaternary ammonium or phosphonium salts, wherein the four hydrocarbon residues are same or different and each is independently selected from the group consisting of C$_1$-C$_6$-alkyl and aralkyl whereby the total number of carbon atoms in the four substituents ranges from 6 to 30.

Most preferred are the tetra(C$_2$-C$_6$-alkyl)ammonium salts, especially the tetrabutylammonium salt of 1H-1,2,4-triazole or 1H-imidazole.

The reaction according to the invention is carried out in the presence or absence of a suitable solvent and/or diluent. In a preferred embodiment of the invention the reaction is carried out in the presence of a solvent, which is selected from nonpolar to aprotic dipolar, reaction-inert, organic solvents.

Illustrative examples for suitable solvents or diluents are aliphatic or aromatic hydrocarbons, such as petroleum ether, hexane, cyclohexane, benzene, toluene, xylenes; ethers and ethereal compounds, such as dialkyl ethers, diethylether, diisopropyl ether, tert.-butylmethylether, dioxan, tetrahydrofurane; nitriles, such as acetonitrile, propionitrile, benzonitril; N,N-dialkylated amides, such as dimethyl formamide, diethyl formamide, dimethylacetamide; sulphoxides, such as dimethyl sulphoxide, and mixtures of such solvents, if suitable.

For practical use aromatic solvents are preferred. Toluene is most preferred, due to its easy recoverability and low toxicity.

The temperatures in the above described substitution reaction range from 30° to 110° C., preferably from 60° to 90° C.

In a lower temperature range beyond 30° the reactivity becomes too slow, and at elevated temperatures exceeding 110° C. the quaternary salts tend to decompose.

The quaternary ammonium and phosphonium salts of 1H-1,2,4-triazole or 1H-imidazole, respectively, can be prepared by reaction of the desired azole with a quaternary ammonium or phosphonium hydroxide of the following formula $$R_{11}-\overset{R_8}{\underset{R_{10}}{Z^{\oplus}}}-R_9 \ OH^{\ominus}$$

wherein Z, $R_8$, $R_9$, $R_{10}$ and $R_{11}$ are as defined hereinabove, or by reaction of a corresponding quaternary ammonium or phosphonium halide, preferably chloride or bromide with either 1H-1,2,4-triazole or 1H-imidazole, respectively, in the presence of an alkaline metal hydroxide:

$$R_{11}-\overset{R_8}{\underset{R_{10} \ [\text{or Hal}^{\ominus}]}{Z^{\oplus}}}-R_9 \ OH^{\ominus} + HN\underset{X}{\overset{/=N}{\diagdown_{N=}}} \xrightarrow[\text{[or } -\text{HalH]}]{\text{(hydroxide)} \ -H_2O}$$

$$R_{11}-\overset{R_8}{\underset{R_{10}}{Z^{\oplus}}}-R_9 \ ^{\ominus}|N|\underset{X}{\overset{/=N}{\diagdown_{N=}}}$$

It is advantageous to remove the water formed at the reaction e.g. by azeotropic destillation or by dry freezing in high vakuum.

The quaternary ammonium and phosphonium salts of 1H-1,2,4-triazole and 1H-imidazole are solid, waxy or highly viscous materials soluble in a number of common organic solvents.

The following examples serve to illustrate the process of manufacture. It should be noted, however, that the invention is not limited to the particular embodiments therein. Various modifications thereof can be employed and will be readily apparent to those skilled in the art.

In the following examples the temperature values are expressed in degrees Centigrade. Unless otherwise indicated the percentage is by weight.

EXAMPLES OF CHEMICAL PREPARATION

A. Preparation of the precursor products

EXAMPLE A

Preparation of $$^{\oplus}N(C_4H_9\text{-}n)_4 \ ^{\ominus}|N|\underset{N=}{\overset{/=N}{\diagdown}}$$

tetrabutylammonium 1H-1,2,4-triazole:

7 g of 1H-1,2,4-triazole were dissolved in 65 g of a commercial 40% aqueous solution of tetrabutylammonium hydroxide. The mixture was evaporated in vacuo and 50 ml portions of toluene were added several times to remove the water obtained azeotropically. Finally the viscous product was dried in high vacuum until constant in weight. There was obtained 31.5 g of a yellowish, viscous mass.

EXAMPLE B

Preparation of $$CH_3-N^{\oplus}(C_8H_{17}\text{-}n)_3 \ ^{\ominus}|N|\underset{N=}{\overset{/=N}{\diagdown}}$$

methyltricaprylammonium 1H-1,2,4-triazole:

A mixture of 5.6 g potassium hydroxide and 7 g of 1H-1,2,4-triazole in 150 ml ethanol was heated on the steam bath until a clear solution resulted. 41 g of methyltricaprylammoniumchloride (="Aliquat 336") were added and the heating was continued for 5 to 10 minutes. The white potassium chloride precipitation was filtered off and the clear solution was evaporated in vacuo. There was obtained 44.5 g of a pale yellow viscous oil.

B. Preparation of compounds of the formula I

EXAMPLE 1:

Preparation of (1.9)

$$(CH_3)_3C\diagdown_{\underset{O}{\overset{O}{\diagup}}}C-CH-O-\underset{}{\diagup}\diagdown-Cl$$
(with triazole N substituent)

2-tert.-butyl-2[1-(4-chlorophenoxy)-1-(1H-1,2,4-triazole-1-yl]-methyl-1,3-dioxolane Tetrabutylammonium 1H-1,2,4-triazole prepared from 7 g of 1H-1,2,4-triazole and 65 g 40% aqueous tetrabutylammonium hydroxide as described above, was dissolved in 200 ml dry dioxane and 24.5 g of 2-tert.-butyl-2[1-bromo(4-chlorphenoxy)]-methyl-1,3-dioxolane were added in portions with stirring. The temperature was set to 80°-85° and stirring was continued for 3 hours. The mixture was concentrated in vacuo to remove most of the dioxan and shaken with 200 ml of 0.5 N hydrochloric acid and diethylether.

The etheral solution was washed with water, dried and evaporated to yield 17 g of white crystals mp. 98°-100° which after crystallization from hexan melted at 103°-105°. 2 g of a product melting at 160°-165° and insoluble in diethylether were obtained by filtering the biphasic mixture during workup, this product being the 1H-1,3,4-triazol-1-yl isomer.

EXAMPLE 2

Preparation of

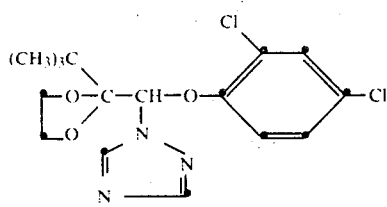
(1.10)

2-tert.-butyl-2[1-(2,4-dichlorophenoxy)-1-(1H-1,2,4-triazole-1-yl)]-methyl-1,3-dioxalane 185 g of tetrabutylammonium 1H-1,2,4-triazole were stirred with 300 ml of toluene at 90°. A solution of 135 g of 2-tert.-butyl-2[1-bromo-1-(2,4-dichlorophenoxy)]-methyl-1,3-dioxalane in 150 ml of toluene was added during 30 minutes. The mixture was stirred at the same temperature for 4 hours. After cooling to room temperature it was shaken with 400 ml of 0.2 N hydrochlorid acid, the toluene layer was additionally extracted with water. Between the phases the white solid 1H-1,3,4-triazol-1-yl isomer separated as by-product, which after solution yielded 20 g of white crystals mp. 118°–120°.

The toluene solution was evaporated and the resulting pale yellow oil triturated with hexane. 120 g of the desired end product were obtained, mp. 106°–108°; white crystals.

EXAMPLE 3

Preparation of

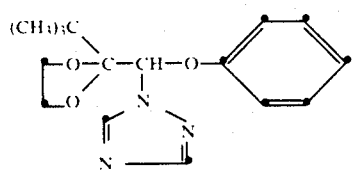
(1.7)

2-tert.-butyl-2[1-phenoxy-1-(1H-1,2,4-triazole-1-yl)]-methyl-1,3-dioxolane

A mixture of 3.7 g 1H-1,2,4-triazole and 51 g of 20% aqueous tetrapropylammonium hydroxide was evaporated to dryness. The solid quaternary ammonium salt was added to a solution of 10.5 g of 2-(1-bromo-1-phenoxy)-methyl-2-tert.-butyl-1,3-dioxolane in 150 ml of benzene. The mixture was stirred at 60° for 12 hours and then extracted three times with 50 ml of water. The benzene layer was evaporated to yield 9 g of a viscous oil, which was purified over a silica column using diethylether as eluant. This procedure provided 4.2 g of pure product as a colorless viscous oil.

The following compounds according to formula I were prepared by procedures analogous to the foregoing examples.

TABLE 1

$$A = -CH-CH-$$
$$\quad\quad | \quad |$$
$$\quad\quad R_4 \quad R_5$$

| Comp. No. | $R_1$ | $R_2$ | $R_3$ | $R_4$ | $R_5$ | X | Physical data |
|---|---|---|---|---|---|---|---|
| 1.1 | 4-Cl | H | H | H | H | CH | mp. 102–104° |
| 1.2 | 2-Cl | 4-Cl | H | H | H | CH | mp. 249–251°(as HCl salt) |
| 1.3 | H | H | H | H | H | CH | visc. oil |
| 1.4 | 2-Cl | 4-Cl | H | $C_2H_5$ | H | CH | mp. 166–168°(as $HNO_3$ salt) |
| 1.5 | 4-$C_6H_5$ | H | H | $C_2H_5$ | H | CH | visc. oil |
| 1.6 | 4-Cl | H | H | $CH_3$ | $CH_3$ | CH | visc. oil |
| 1.7 | H | H | H | H | H | N | visc. oil |
| 1.8 | 4-F | H | H | H | H | N | visc. oil |
| 1.9 | 4-Cl | H | H | H | H | N | mp. 103–105° |
| 1.10 | 2-Cl | 4-Cl | H | H | H | N | mp. 106–108° |
| 1.11 | 4-Cl | H | H | $C_2H_5$ | H | N | mp. 110–115° |
| 1.12 | 4-Cl | H | H | $C_3H_7(n)$ | H | N | mp. 90–92° |
| 1.13 | 4-Cl | H | H | $CH_3$ | $CH_3$ | N | visc. oil |
| 1.14 | 2-Cl | 4-Cl | H | $C_2H_5$ | H | N | visc. oil |
| 1.15 | 4-$C_6H_5$ | H | H | $C_2H_5$ | H | N | visc. oil |
| 1.16 | 2-Cl | 4-Cl | H | $-CH_2OCH_3$ | H | N | sticky solid (gum) |
| 1.17 | 4-Cl | H | H | $-CH_2OC_6H_5$ | H | N | visc. oil |
| 1.18 | 4-Cl | H | H | $-CH_2CH_2CH_2CH_2-$ | | N | mp. 115–120° |

TABLE 2

$$A = -CH_2-C-CH_2-$$
$$\quad\quad\quad / \quad \backslash$$
$$\quad\quad R_6 \quad\quad R_7$$

| Comp. | $R_1$ | $R_2$ | $R_3$ | $R_6$ | $R_7$ | X | Physical data |
|---|---|---|---|---|---|---|---|
| 2.1 | 4-Cl | H | H | H | H | N | mp. 55–57° |
| 2.2 | 4-Cl | H | H | $CH_3$ | $CH_3$ | N | visc. oil |

What we claim is:

1. A process for the preparation of a compound of the formula I,

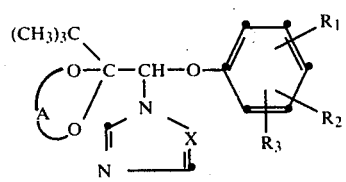
(I)

wherein

X represents —CH= or —N=;

$R_1$, $R_2$ and $R_3$ are each independently selected from the group consisting of hydrogen, halogen, lower alkyl, cyano, methoxy, phenyl and nitro; A represents $-CH(R_4)-CH(R_5)-$ or $-CH_2-C(R_6)(R_7)-CH_2-$; $R_4$ and $R_5$ are each independently selected from the group consisting of hydrogen, $C_1$-$C_6$-alkyl, $C_1$-$C_6$-alkoxymethyl and phenoxymethyl or said substituents $R_4$ and $R_5$ form together a tetramethylene group; and $R_6$ and $R_7$ are independently selected from the group consisting of hydrogen or lower alkyl, which process comprises reacting a compound of formula III,

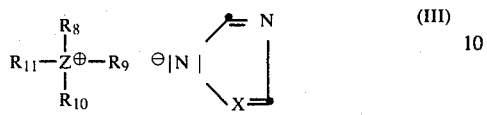   (III)

wherein X represents —CH= or —N=; Z represents nitrogen or phosphorus; $R_8$, $R_9$, $R_{10}$ and $R_{11}$ are the same or different and are each independently selected from the group consisting of $C_1$-$C_{18}$-alkyl, aralkyl, aryl and aryloxyalkyl at a temperature of from 30° to 110° C. with the compound of the formula II,

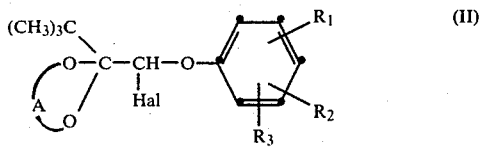   (II)

wherein A, $R_1$, $R_2$ and $R_3$ have the previously defined meanings and Hal represents halogen.

2. A process according to claim 1 wherein X represents nitrogen.

3. A process according to claim 1 or 2 wherein Z represents nitrogen.

4. A process according to any one of claims 1 to 3 wherein $R_8$, $R_9$, $R_{10}$ and $R_{11}$ are the same or different and are each independently selected from the group consisting of $C_1$-$C_{18}$-alkyl and aralkyl.

5. A process according to claim 4 wherein said substituents $R_8$, $R_9$, $R_{10}$ and $R_{11}$ are the same or different and are each independently selected from the group consisting of $C_1$-$C_6$-alkyl and aralkyl whereby the total number of carbon atoms in the four substituents ranges from 6 to 30.

6. A process according to any one of claims 1 to 5 wherein the temperature ranges from 60° to 90° C.

7. A process according to any one of claims 1 to 6, wherein the process is performed in the presence of a non polar to aprotic dipolar, reaction-inert organic solvent.

8. An improved process for the preparation of a compound according to formula I,

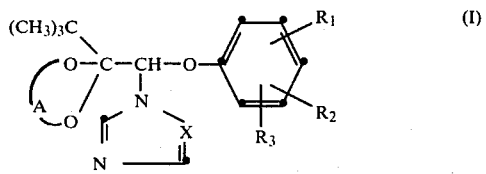   (I)

wherein
X represents —CH= or —N=;
$R_1$, $R_2$ and $R_3$ are each independently selected from the group consisting of hydrogen, halogen, lower alkyl, cyano, methoxy, phenyl and nitro; A represents —CH($R_4$)—CH($R_5$)— or —CH$_2$—C($R_6$)($R_7$)—CH$_2$—;
$R_4$ and $R_5$ are each independently selected from the group consisting of hydrogen, $C_1$-$C_6$-alkyl, $C_1$-$C_6$-alkoxymethyl and phenoxymethyl or said substituents $R_4$ and $R_5$ form together a tetramethylen group; and $R_6$ and $R_7$ are each independently selected from the group consisting of hydrogen and lower alkyl, by the reaction of an azolium anion of the formula

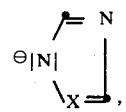

wherein X represents —CH= or —N=, with a compound of the formula II

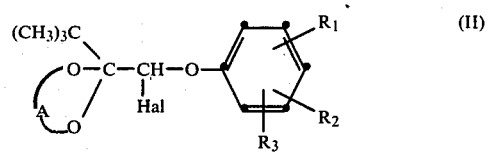   (II)

wherein A, $R_1$, $R_2$ and $R_3$ have the previously defined meanings and Hal represents halogen, the improvement which comprises reacting said compound of the formula II at a temperature of from 30° to 110° centigrades with an azolium anion in the form of the formula III,

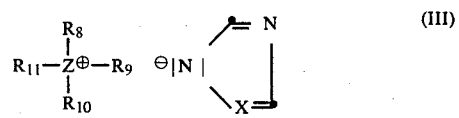   (III)

wherein X represents —CH= or —N=; Z represents nitrogen or phosphorus; $R_8$, $R_9$, $R_{10}$ and $R_{11}$ the same or different and are each independently selected from the group consisting of $C_1$-$C_{18}$-alkyl, aralkyl, aryl and aryloxyalkyl, thereby splitting off a compound of the following formula

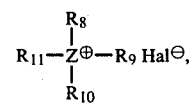

wherein Z, $R_8$, $R_9$, $R_{10}$, $R_{11}$ and Hal are as defined hereinabove.

9. In the process according to claim 8 whereby a non polar to aprotic dipolar, reaction-inert organic solvent is used.

10. In a process according to claims 8 or 9 whereby X represents nitrogen.

11. In the process according to any one of claims 8 to 10 whereby Z represents nitrogen.

12. In the process according to any one of claims 8 to 11 whereby $R_8$, $R_9$, $R_{10}$ and $R_{11}$ are the same or different and are each independently selected from the group consisting of $C_1$-$C_{18}$-alkyl and aralkyl.

13. In the process according to claim 12 whereby said substituents $R_8$, $R_9$, $R_{10}$ and $R_{11}$ are the same or different and each are independently selected from the group consisting of $C_1$-$C_6$-alkyl and aralkyl whereby the total number of carbon atoms in the four substituents ranges from 6 to 30.

14. In a process according to any one of claims 8 to 13 whereby said process is performed at a temperature of from 60° to 90° centigrades.

* * * * *